United States Patent
Freeberg

(10) Patent No.: US 7,647,108 B2
(45) Date of Patent: Jan. 12, 2010

(54) METHODS AND SYSTEMS FOR SELECTION OF CARDIAC PACING ELECTRODE CONFIGURATIONS

(75) Inventor: Scott M. Freeberg, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 581 days.

(21) Appl. No.: 10/955,393

(22) Filed: Sep. 30, 2004

(65) Prior Publication Data

US 2006/0074454 A1    Apr. 6, 2006

(51) Int. Cl.
*A61N 1/365* (2006.01)
(52) U.S. Cl. .......................................... 607/28
(58) Field of Classification Search ..................... 607/28
See application file for complete search history.

(56) References Cited

U.S. PATENT DOCUMENTS

| 4,573,481 A | 3/1986 | Bullara |
| 5,033,467 A | 7/1991 | Bocchi et al. |
| 5,203,348 A | 4/1993 | Dahl et al. |
| 5,230,337 A | 7/1993 | Dahl et al. |
| 5,301,677 A | 4/1994 | Hsung |

(Continued)

FOREIGN PATENT DOCUMENTS

WO    WO2004091720    10/2004

OTHER PUBLICATIONS

U.S. Appl. No. 11/114,569, filed Apr. 26, 2005, Sathaye.

(Continued)

*Primary Examiner*—Angela D Sykes
*Assistant Examiner*—Amanda Patton
(74) *Attorney, Agent, or Firm*—Hollingsworth & Funk, LLC

(57) ABSTRACT

Methods and systems involve selecting lead configurations in a pulse generator capture verification system. Capture threshold data is collected from at least one alternative electrode configuration. The capture threshold data from the at least one alternative electrode configuration is compared with capture threshold data collected using a primary electrode configuration. A pacing electrode configuration is selected based on the comparison. Backup safety pacing is provided using the primary electrode configuration.

14 Claims, 5 Drawing Sheets

U.S. PATENT DOCUMENTS

| | | | |
|---|---|---|---|
| 5,350,410 A * | 9/1994 | Kleks et al. | 607/28 |
| 5,360,442 A | 11/1994 | Dahl et al. | |
| 5,366,496 A | 11/1994 | Dahl et al. | |
| 5,372,606 A | 12/1994 | Lang et al. | |
| 5,391,200 A | 2/1995 | KenKnight et al. | |
| 5,397,342 A | 3/1995 | Heil, Jr. et al. | |
| 5,411,525 A | 5/1995 | Swanson et al. | |
| 5,431,693 A | 7/1995 | Schroeppel | |
| 5,443,485 A | 8/1995 | Housworth et al. | |
| 5,468,254 A | 11/1995 | Hahn et al. | |
| 5,545,186 A | 8/1996 | Olson et al. | |
| 5,545,202 A | 8/1996 | Dahl et al. | |
| 5,591,216 A | 1/1997 | Testerman et al. | |
| 5,603,732 A | 2/1997 | Dahl et al. | |
| 5,634,938 A | 6/1997 | Swanson et al. | |
| 5,658,318 A | 8/1997 | Stroetmann et al. | |
| 5,674,254 A | 10/1997 | van Krieken | |
| 5,683,431 A | 11/1997 | Wang | |
| 5,697,956 A | 12/1997 | Bornzin | |
| 5,718,720 A | 2/1998 | Prutchi et al. | |
| 5,735,883 A | 4/1998 | Paul et al. | |
| 5,855,593 A | 1/1999 | Olson et al. | |
| 5,916,243 A | 6/1999 | KenKnight et al. | |
| 6,076,015 A | 6/2000 | Hartley et al. | |
| 6,141,581 A | 10/2000 | Olson et al. | |
| 6,148,234 A | 11/2000 | Struble | |
| 6,221,011 B1 | 4/2001 | Bardy | |
| 6,259,947 B1 | 7/2001 | Olson et al. | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,360,127 B1 | 3/2002 | Ding et al. | |
| 6,363,281 B1 | 3/2002 | Zhu et al. | |
| 6,368,284 B1 | 4/2002 | Bardy | |
| 6,398,728 B1 | 6/2002 | Bardy | |
| 6,434,428 B1 | 8/2002 | Sloman et al. | |
| 6,438,410 B2 | 8/2002 | Hsu et al. | |
| 6,440,066 B1 | 8/2002 | Bardy | |
| 6,487,443 B2 | 11/2002 | Olson et al. | |
| 6,493,586 B1 | 12/2002 | Stahmann et al. | |
| 6,512,953 B2 | 1/2003 | Florio et al. | |
| 6,597,951 B2 | 7/2003 | Kramer et al. | |
| 6,611,712 B2 | 8/2003 | Spinelli et al. | |
| 6,615,089 B1 | 9/2003 | Russie et al. | |
| 6,640,136 B1 | 10/2003 | Helland et al. | |
| 6,708,058 B2 | 3/2004 | Kim et al. | |
| 6,731,985 B2 | 5/2004 | Bradley et al. | |
| 6,738,668 B2 | 5/2004 | Mouchawar et al. | |
| 6,772,008 B2 | 8/2004 | Zhu et al. | |
| 6,915,160 B2 | 7/2005 | Auricchio et al. | |
| 6,915,164 B2 | 7/2005 | Bradley et al. | |
| 6,978,178 B2 * | 12/2005 | Sommer et al. | 607/28 |
| 6,993,389 B2 | 1/2006 | Ding et al. | |
| 7,031,773 B1 * | 4/2006 | Levine et al. | 607/28 |
| 7,062,327 B2 | 6/2006 | Bradley et al. | |
| 7,194,313 B2 | 3/2007 | Libbus | |
| 7,233,821 B2 | 6/2007 | Hettrick et al. | |
| 7,299,093 B2 | 11/2007 | Zhu et al. | |
| 7,319,900 B2 | 1/2008 | Kim et al. | |
| 7,337,000 B2 | 2/2008 | Meyer et al. | |
| 7,392,086 B2 | 6/2008 | Sathaye | |
| 7,499,751 B2 | 3/2009 | Meyer et al. | |
| 2002/0133203 A1 | 9/2002 | Mouchawar et al. | |
| 2004/0064162 A1 * | 4/2004 | Manrodt et al. | 607/28 |
| 2004/0116971 A1 | 6/2004 | Bjorling et al. | |
| 2004/0215253 A1 * | 10/2004 | Weinberg | 607/9 |
| 2004/0230229 A1 | 11/2004 | Lovett et al. | |
| 2005/0060002 A1 | 3/2005 | Zhu et al. | |
| 2005/0060007 A1 | 3/2005 | Goetz | |
| 2005/0131477 A1 | 6/2005 | Meyer et al. | |
| 2006/0247693 A1 | 11/2006 | Dong et al. | |
| 2006/0247695 A1 | 11/2006 | Stalsberg et al. | |
| 2006/0247707 A1 | 11/2006 | Meyer et al. | |
| 2008/0294215 A1 | 11/2008 | Sathaye | |
| 2008/0300644 A1 | 12/2008 | Sathaye | |
| 2009/0043352 A1 | 2/2009 | Brooke et al. | |

OTHER PUBLICATIONS

U.S. Appl. No. 11/520,879, filed Sep. 14, 2006, Brooke et al.
U.S. Appl. No. 11/890,668, filed Aug. 7, 2007, Sathaye et al.

* cited by examiner

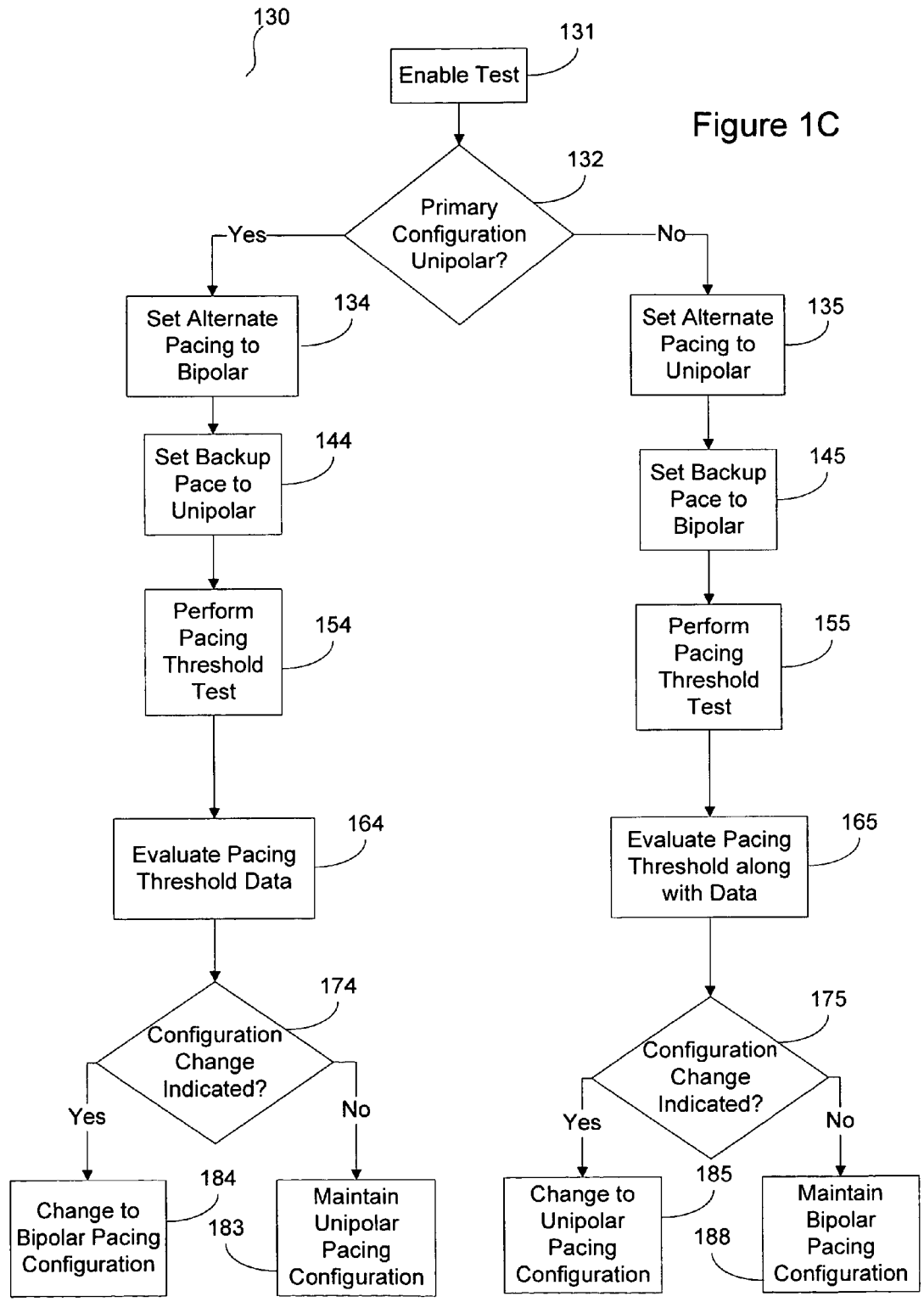

METHODS AND SYSTEMS FOR SELECTION OF CARDIAC PACING ELECTRODE CONFIGURATIONS

FIELD OF THE INVENTION

The present invention relates generally to cardiac therapy devices and more particularly to selecting cardiac electrode configurations for delivering pace pulses.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to produce a contraction. The electrical cardiac signal following the contraction is denoted the captured response (CR). It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter. Capture threshold detection allows the cardiac rhythm management system to adjust the energy level of pace pulses that correspond to an energy expenditure that reliably produces capture while preserving battery life.

SUMMARY OF THE INVENTION

Various embodiments of present invention involve methods and systems for delivering pace pulses that reliably produce capture while lowering energy expenditure. In accordance with one embodiment, a method involves selecting an electrode configuration for pacing. The method includes collecting capture threshold data from an alternative pacing electrode configuration. The capture threshold data from the alternative pacing electrode configuration is compared with capture threshold data collected using a primary pacing electrode configuration. A pacing electrode configuration is selected based on the comparison. Various processes of the method may be performed implantably. For example, two or more of collecting, comparing and selecting may be performed implantably.

According to one aspect of the invention, additional data may be collected, such as lead impedance data and/or cardiac signal amplitude data, e.g., P-wave or R-wave amplitude data. The pacing electrode configuration may be selected using the additional data.

Another embodiment of the invention is directed to a system for selecting a pacing electrode configuration. The system includes a plurality of electrodes configured to electrically couple to a heart. The plurality of electrodes are configurable to include a primary pacing electrode configuration and at least one alternative pacing electrode configuration. The electrodes are coupled to a pulse generator configured to deliver electrical stimulation pulses to the heart using configurations of the plurality of electrodes. A processor collects capture threshold data associated with the at least one alternative pacing electrode configuration. A processor compares the capture threshold data from the alternative pacing electrode configuration with capture threshold data collected using the primary pacing electrode configuration, and selects a pacing electrode configuration based on the comparison.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1B-1C are flowcharts illustrating methods for selecting pacing electrode configurations in accordance with embodiments of the invention;

Figure 1A:
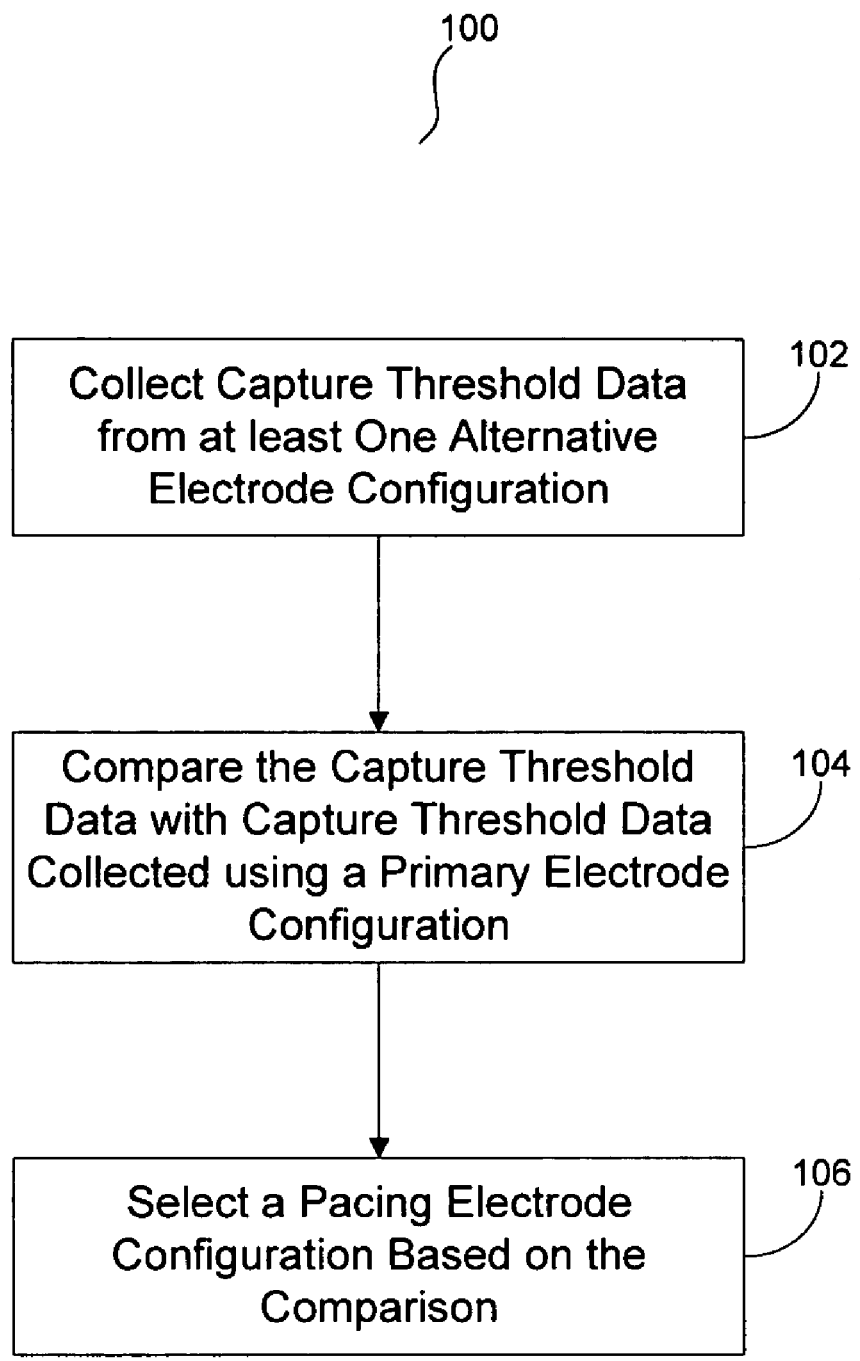
FIG. 1A is a flowchart of a method for selecting pacing electrode configurations that can deliver pace pulses which reliably produce capture while lowering energy expenditure in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Embodiments of the invention are directed towards methods and systems for selecting an electrode configuration for pacing. The selection of a pacing electrode configuration involves determining an electrode configuration that reliably produces capture while lowering energy expenditure. Selection of an electrode configuration for pacing can be based on capture threshold data acquired during capture threshold testing. Processes in accordance with embodiments of the invention can be used to safely determine pacing capture thresholds in various electrode configurations, including electrode configurations involving a single heart chamber or multiple heart chambers. The processes described herein may be employed to select pacing electrode configurations used in the treatment of congestive heart failure, including, for example, cardiac resynchronization therapy including bi-ventricular and/or bi-atrial pacing.

Those skilled in the art will appreciate that reference to a capture threshold testing procedure indicates a method of determining the capture threshold in one or more of left atrium, right atrium, left ventricle, and right ventricle. In such a procedure, a cardiac rhythm management (CRM) system, or other device, automatically or upon command, initiates a search for the capture threshold of the selected heart chamber or chambers. The capture threshold is defined as the lowest pacing energy that consistently captures the heart.

It should be noted that capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. If a predetermined number of pace pulses delivered during normal pacing do not produce a captured response, the pacemaker may initiate a capture threshold test to determine the capture threshold.

The capture threshold testing procedures described in connection with the exemplary embodiments can be initiated, for example, automatically by an implantable CRM system, automatically by a remote patient management systems, and/or manually by a user. In one example of a capture threshold testing procedure, the pacemaker automatically delivers a sequence of pacing pulses to the heart and detects the cardiac responses to the pace pulses. A backup pace is delivered after each pacing pulse. For example, the backup pace may be delivered about 100 msec after the initial pace. The energy of the pacing pulses may be decreased in discrete steps until a predetermined number of loss-of-capture events occur. The pacemaker may increase the stimulation energy in discrete steps until a predetermined number of capture events occur to confirm the capture threshold. Other procedures for implementing capture threshold testing may be utilized. In one example, the pacing energy may be increased in discrete steps until capture is detected. In another example, the pacing energy during the test may be varied according to a binomial search pattern.

Capture threshold testing, in accordance with embodiments of the invention, may be performed using a variety of cardiac electrode configurations. Data obtained from capture threshold testing using the various electrode configurations can be compared and used to select an appropriate pacing electrode configuration.

In addition to capture threshold data, selection of a pacing electrode configuration can be based on other data relevant to the electrode configuration. Other data relevant to electrode selection may include, for example, lead impedance data, P wave amplitude data and/or R wave amplitude data. Data collected using the various electrode configurations can be compared and used to select a particular pacing electrode configuration. For example, an electrode configuration may be selected that delivers a pacing energy that reliably produces capture while lowering energy expenditure, in accordance with the present invention.

FIG. 1A is a flowchart of a method 100 for selecting a pacing electrode configuration in accordance with embodiments of the invention. Capture threshold data is collected 102 from at least one alternative electrode configuration. Capture threshold data collected 102 from the alternative electrode configuration is compared 104 with capture threshold information from a primary electrode configuration. A pacing electrode configuration is selected 106 based on the comparison of the capture threshold data from the alternative and the primary electrode configurations.

Initiation of a capture threshold test to collect the capture threshold data for pacing electrode selection can be automatically or manually triggered. In some embodiments, pacing electrode selection may be performed implantably, for example, by the CRM. Implantably performing an operation comprises performing the operation using a component, device, or system that is partially or fully implanted within the body. In other embodiments, capture threshold data for the various electrode configurations may be transferred to a remote device and the pacing electrode selection may be performed external to the patient.

Figure 1B:
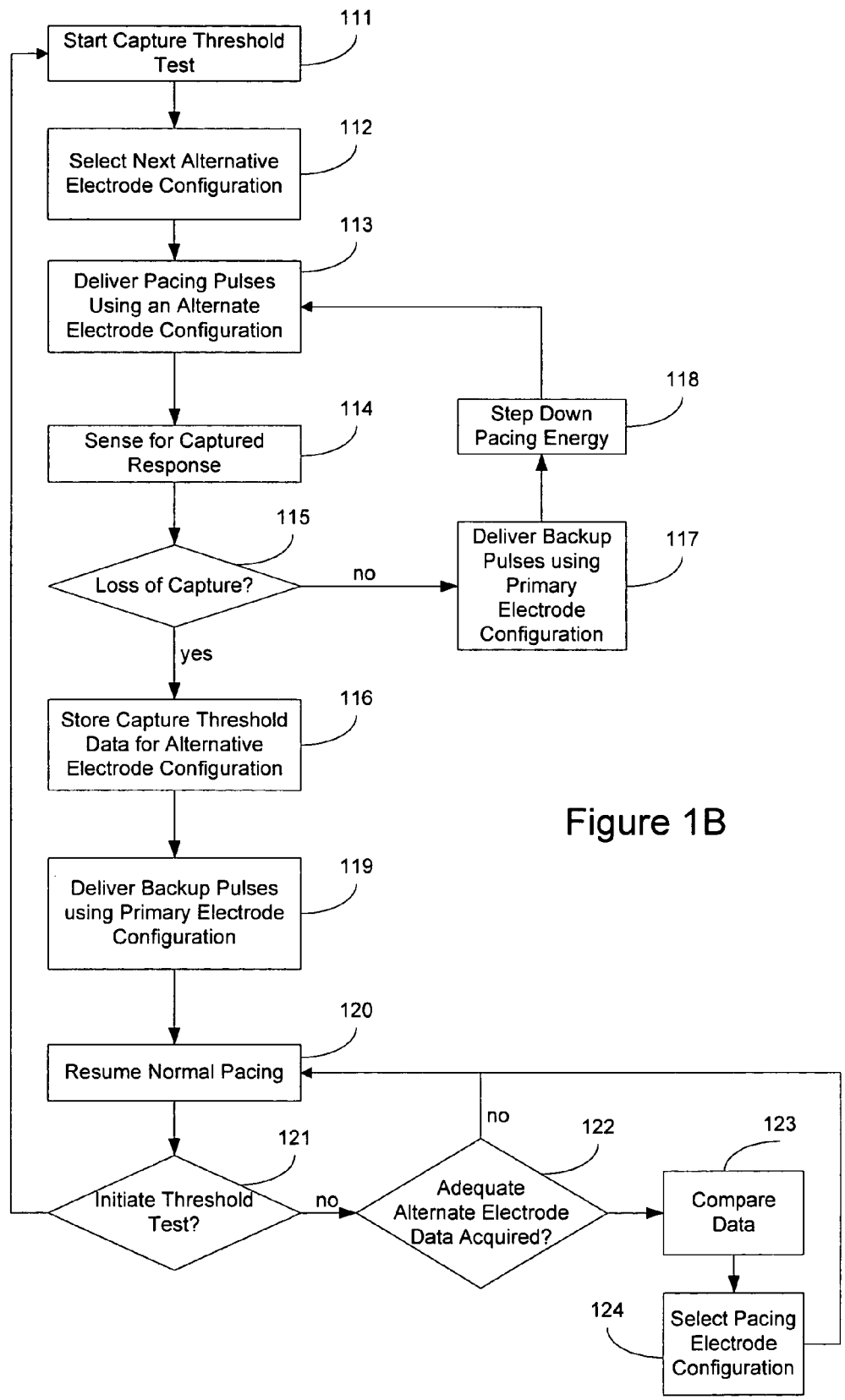

FIG. 1B illustrates a method 110 for selecting a pacing electrode configuration in accordance with an embodiment of the invention. A primary pacing electrode configuration is identified, for example, during device initialization or through other processes. Capture threshold data is acquired for the primary pacing electrode configuration. Upon commencement 111 of the capture threshold test, an alternate pacing electrode configuration, different from the primary configuration, is selected 112. The pacing output utilizes the selected alternate electrode configuration for the duration of the test. Alternate electrode configurations may comprise one or more electrodes disposed within, on, or about the same heart chamber as a primary electrode. Alternate electrode configurations may comprise one or more electrodes disposed within, on, or about a different heart chamber as the primary electrode. The primary and/or alternate electrode configurations may comprise bipolar and/or unipolar configurations in single and/or multi-chamber and heart chambers.

The pacing pulses of the capture threshold test are delivered 113 using the selected alternate electrode configuration. Following the delivery of each pacing pulse, the system senses 114 for a captured response. If the pacing pulse captures the heart, the pacing energy is stepped down. The next pacing pulse is delivered 113 at the stepped-down pacing energy using the alternate electrode configuration.

Loss of capture may be detected if x out of y pacing pulses do not produce a captured response. If loss of capture is detected 115, then the capture threshold associated with the alternate electrode configuration is stored 116. Various techniques for detecting capture and/or other cardiac responses to pacing, aspects of which may be utilized in pacing electrode selection according to embodiments of the present invention, are described in commonly owned U.S. patent application Ser. No. 10/335,599, filed Dec. 31, 2002, Ser. No. 10/335, 534, filed Dec. 31, 2002, Ser. No. 10/733,869, filed Dec. 11, 2003, S/N 10,10/734,599, filed Dec. 12, 2003, and Ser. No. 10/735,519, filed Dec. 12, 2003 all of which are incorporated herein by reference.

A backup pacing pulse is delivered 117, 119 after a capture sensing window for each pacing pulse delivered, for example, within about 100 msec following delivery of the pacing pulse. The backup pace is delivered on a default pacing vector with known characteristics to reduce the risk of therapy interruptions. In some embodiments backup paces are delivered 117, 119 using the primary electrode configuration. In other embodiments the primary pacing electrode configuration may be different from the backup pacing configuration. For example, some implementations involve pacing the left ventricle using an alternate left ventricular (LV) electrode configuration that is different from the primary LV electrode configuration. However, the backup pace may be delivered to the right ventricle using a right ventricular pacing vector. Backup pacing using the default pacing vector with predictable characteristics promotes therapy delivery while determining the pacing capture threshold in alternate lead configurations.

After the capture threshold of the selected alternate electrode configuration is determined and stored 116, normal pacing resumes 120. A number of candidate alternate electrode configurations may be tested before a pacing electrode configuration selection is made. A subsequent capture threshold test may collect data for the next alternate electrode configuration. Capture threshold testing can be programmed to automatically initiate, for example, every 21 hours.

When a sufficient amount of capture threshold data has been collected for the candidate electrode configurations, a pacing electrode selection is performed. Selection of the pacing electrode configuration may involve, for example, comparison of the capture threshold data acquired from a candidate electrode configuration to the primary capture threshold data. Additionally, the capture threshold data of the candidate electrode configurations may be compared. The pacing electrode configuration may be selected, for example, that requires a lower pacing energy and reliably produces capture.

FIG. 1C is a further illustration of a method 130 for selecting pacing electrode configurations in accordance with embodiments of the invention. The capture threshold test is initiated 131, for example, either automatically by the CRM system or other system, or manually. If the primary configuration is unipolar 132, the alternate electrode configuration used for the capture threshold test is a bipolar configuration 134. Backup pacing uses the primary unipolar configuration 144.

Alternatively, if the primary configuration is bipolar 132, the alternate electrode configuration used for the capture threshold test is a unipolar configuration 135. Backup pacing is set to the primary bipolar pacing electrode configuration 145.

Backup pacing ensures the patient receives therapy during the capture threshold test, thereby allowing safe acquisition of pacing threshold information from electrode configurations other than the primary configuration. The capture threshold test is performed 154, 155 for the alternate electrode configuration. Capture threshold data is evaluated 164, 165 and a determination is made 174,175 as to whether the primary configuration should be changed based on the evaluation.

In some embodiments, capture threshold data may be evaluated along with other data associated with alternative electrode configurations, such as impedance and signal amplitude data. In these embodiments, capture threshold data, along with other data associated with the alternate electrode configuration may be considered in the selection process.

If a configuration change is indicated 174 and the primary electrode configuration is unipolar, the pacing electrode configuration is changed 184 to bipolar. If no configuration change from the unipolar configuration is indicated 174, the unipolar pacing electrode configuration is maintained 183.

If a configuration change is indicated 175 and the primary electrode configuration is bipolar, the pacing electrode configuration is changed 185 to unipolar. If no change is indicated 175, then the primary pacing electrode configuration is maintained 188.

As discussed in connection with FIG. 1C, the system may operate to select between a primary unipolar and an alternate bipolar pacing configuration or between a primary bipolar configuration and an alternate unipolar configuration. In other implementations, pacing electrode selection may involve selecting between two unipolar configurations or between two bipolar configurations. Alternate electrode configurations may comprise one or more electrodes disposed within, on, or about a different heart chamber as the primary electrode. The primary and/or alternate electrode configurations may comprise bipolar and/or unipolar configurations in single and/or multi-chamber and heart chambers.

The embodiments of the present system illustrated herein are generally described as being implemented in an implantable cardiac rhythm management (CRM) device that may operate in numerous pacing modes known in the art. Various types of single and multiple chamber implantable cardiac defibrillators are known in the art and may be used in connection with the selection of pacing electrode configurations in accordance with methods of the present invention. The methods of the present invention may be implemented in a variety of implantable or patient-external cardiac rhythm management devices, including single and multi chamber pacemakers, defibrillators, cardioverters, bi-ventricular pacemakers, and cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 2:
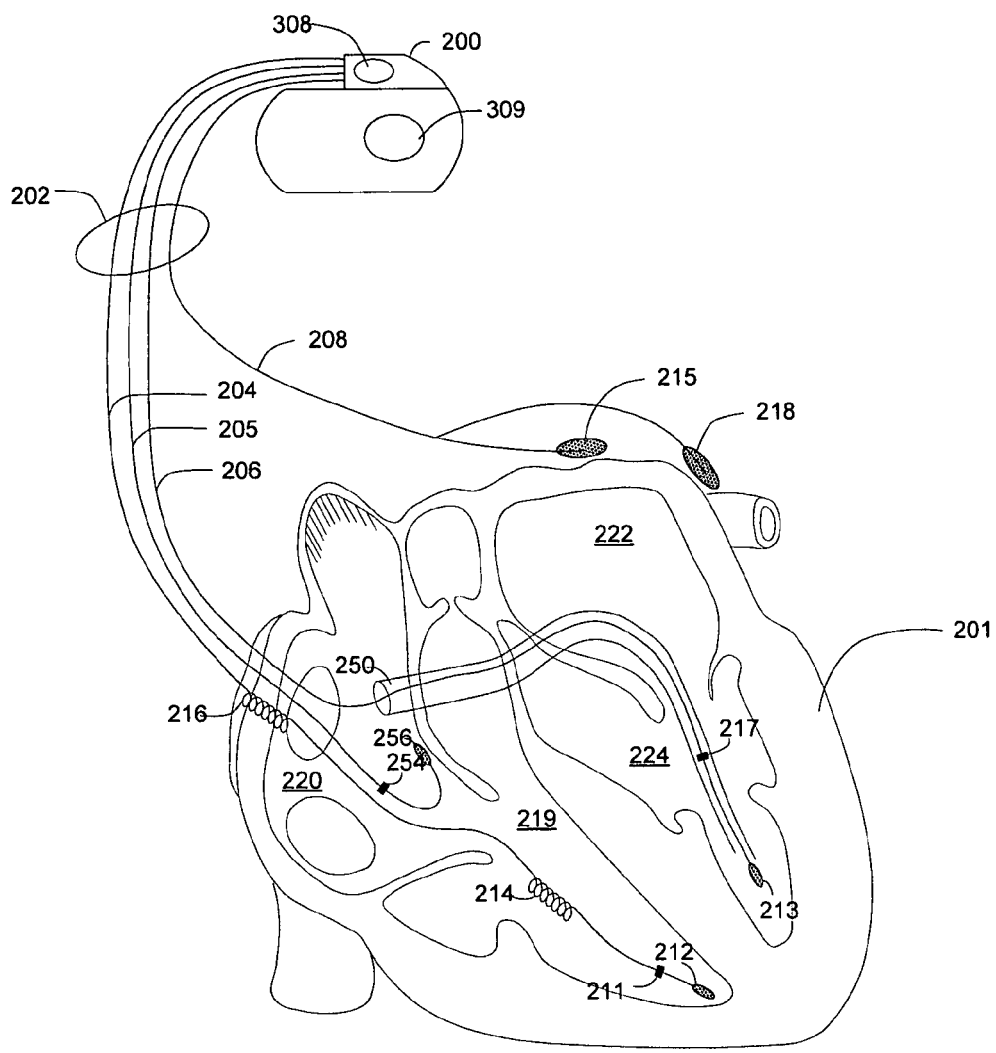
FIG. 2 is a partial view of one embodiment of an implantable medical device in accordance with embodiments of the invention.

Referring now to FIG. 2 of the drawings, there is shown a cardiac rhythm management system that may be used to implement methods for selecting pacing electrode configurations in accordance with embodiments of the invention. The cardiac rhythm management system in FIG. 2 includes a CRM device 200 electrically and physically coupled to a lead system 202. The housing and/or header of the CRM device 200 may incorporate one or more electrodes 308, 309 used to provide electrical stimulation energy to the heart and to sense cardiac electrical activity. The CRM device 200 may utilize all or a portion of the CRM device housing as a can electrode 309. The CRM device 200 may include an indifferent electrode positioned, for example, on the header or the housing of the CRM device 200. If the CRM device 200 includes both a can electrode 309 and an indifferent electrode 308, the electrodes 308, 309 typically are electrically isolated from each other.

The lead system 202 incorporates cardiac electrodes used to detect electric cardiac signals produced by the heart 201 and to provide electrical energy to the heart 201 under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, an intracardiac left ventricular (LV) lead system 206, and an extracardiac left atrial (LA) lead system 208. The lead system 202 of FIG. 2 illustrates one embodiment that may be used in connection with methods for implementing capture threshold tests using alternative lead configurations as described herein.

The lead system 202 may include intracardiac leads 204, 205, 206 implanted in a human body with portions of the intracardiac leads 204, 205, 206 inserted into a heart 201. The intracardiac leads 204, 205, 206 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 2, the lead system 202 may include one or more extracardiac leads 208 having electrodes, e.g., epicardial electrodes, positioned at locations outside the heart for sensing and pacing one or more heart chambers.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium 220 and into the right ventricle 219. In particular, the RV-tip electrode 212, RV-ring electrode 211, and RV-coil electrode 214 are positioned at appropriate locations within the right ventricle 219 for sensing and delivering electrical stimulation pulses to the heart. The SVC-coil 216 is positioned at an appropriate location within the right atrium chamber 220 of the heart 201 or a major vein leading to the right atrial chamber 220 of the heart 201.

In one configuration, the RV-tip electrode 212 referenced to the can electrode 309 may be used to implement unipolar pacing and/or sensing in the right ventricle 219. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle 224 for pacing and/or sensing the left ventricle 224. The left ventricular lead 206 may be guided into the right atrium 220 of the heart via the superior vena cava. From the right atrium 220, the left ventricular lead 206 may be deployed into the coronary sinus ostium, the opening of the coronary sinus 250. The lead 206 may be guided through the coronary sinus 250 to a coronary vein of the left ventricle 224. This vein is used as an access pathway for leads to reach the surfaces of the left ventricle 224 which are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or sensing in the left ventricle may be implemented, for example, using the LV distal electrode referenced to the can electrode 309. The LV distal electrode 213 and the LV proximal electrode 217 may be used together as bipolar sense and/or pace electrodes for the left ventricle. The left ventricular lead 206 and the right ventricular lead 204, in conjunction with the CRM device 200, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 205 includes an A-tip electrode 256 and an A-ring electrode 254 positioned at appropriate locations in the right atrium 220 for sensing and pacing the right atrium 220. In one configuration, the A-tip 256 referenced to the can electrode 309, for example, may be used to provide unipolar pacing and/or sensing in the right atrium 220. In another configuration, the A-tip electrode 256 and the A-ring electrode 254 may be used to effect bipolar pacing and/or sensing.

FIG. 2 illustrates one embodiment of a left atrial lead system 208. In this example, the left atrial lead 208 is implemented as an extracardiac lead with extracardiac electrodes 218 and 215 are electrically coupled to the left atrium at appropriate locations 201 for sensing and pacing the left atrium 222. Unipolar pacing and/or sensing of the left atrium may be accomplished using the extracardiac electrodes, for example, using the extracardiac left atrial electrode 218 to the can 309 pacing vector. Extracardiac left atrial electrodes 215 and 218 may be used together to implement bipolar pacing and/or sensing of the left atrium 222.

Figure 3:
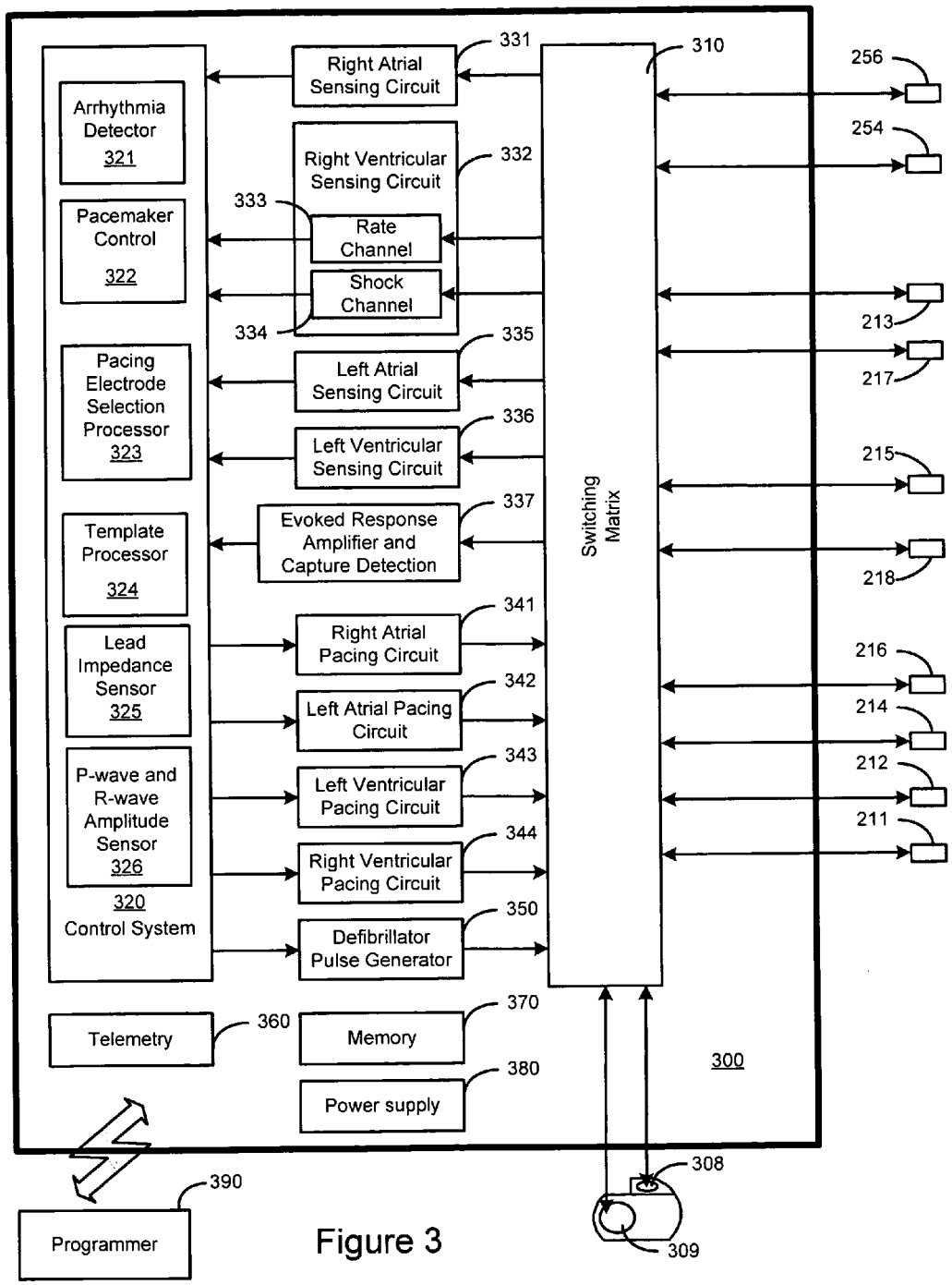
FIG. 3 illustrates an embodiment of a cardiac defibrillator suitable for implementing methods for selecting lead configurations based on pacing capture threshold testing using primary and alternative lead configurations in accordance with embodiments of the present invention.

Referring now to FIG. 3, there is shown an embodiment of a CRM device 300 suitable for implementing methods for selecting lead configurations based on pacing capture threshold testing using primary and alternative lead configurations in accordance with the present invention. FIG. 3 shows a CRM device divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used to describe a cardiac defibrillator suitable for implementing the lead configuration selection methodology of the present invention. In addition, although the CRM device 300 depicted in FIG. 3 contemplates the use of a programmable microprocessor-based logic circuit, other circuit implementations may be utilized.

The CRM device 300 depicted in FIG. 3 includes circuitry for receiving cardiac signals from a heart and delivering electrical stimulation energy to the heart in the form of pacing pulses or defibrillation shocks. In one embodiment, the circuitry of the cardiac defibrillator 300 is encased and hermetically sealed in a housing 301 suitable for implanting in a human body. Power to the cardiac defibrillator 300 is supplied by an electrochemical battery 380. A connector block (not shown) is attached to the housing 301 of the cardiac defibrillator 300 to allow for the physical and electrical attachment of the lead system conductors to the circuitry of the cardiac defibrillator 300.

The CRM device 300 may be a programmable microprocessor-based system, including a control system 320 and a memory 370. The memory 370 may store parameters for various pacing, defibrillation, and sensing modes, along with other parameters. The memory 370 may store information about pacing electrode configurations and capture threshold data associated with various pacing electrode configurations. The memory 370 may be used, for example, for storing historical EGM and therapy data. The historical data storage may include, for example, data obtained from long term patient monitoring used for trending and/or for other diagnostic or therapeutic purposes. Historical data, as well as other information, may be transmitted to an external programmer unit 390 as needed or desired.

The control system 320 and memory 370 may cooperate with other components of the cardiac defibrillator 300 to control the operations of the CRM device 300. The control system depicted in FIG. 3 incorporates a pacing electrode selection processor 323 for selecting electrode configurations based on capture threshold data in accordance with various embodiments of the present invention. The control system 320 may include additional functional components including an arrhythmia detector 321, a pacemaker control circuit 322 a template processor 324, a lead impedance sensor 325, and P-wave and R-wave amplitude sensor 326, along with other components for controlling the operations of the cardiac defibrillator 300.

Telemetry circuitry 360 may be implemented to provide communications between the cardiac defibrillator 300 and an external programmer unit 390. In one embodiment, the telemetry circuitry 360 and the programmer unit 390 communicate using a wire loop antenna and a radio frequency telemetric link, as is known in the art, to receive and transmit signals and data between the programmer unit 390 and the telemetry circuitry 360. In this manner, programming commands and other information may be transferred to the control system 320 of the cardiac defibrillator 300 from the programmer unit 390 during and after implant. In addition, stored cardiac data pertaining to capture thresholds and/or capture detection, for example, along with other data, including data associated with an optimal pacing electrode configuration may be transferred to the programmer unit 390 from the cardiac defibrillator 300.

In the embodiment of the CRM device 300 illustrated in FIG. 3, electrodes A-tip 256, A-ring 254, RV-tip 212, RV-ring 211, RV-coil, SVC-coil, LV distal electrode 213, LV proximal electrode 217, extracardiac left atrial electrodes 215 and 218, indifferent electrode 308, and can electrode 309 are coupled through a switch matrix 310 to sensing circuits 331-337.

A right atrial sensing circuit 331 serves to detect and amplify electrical signals from the right atrium of the heart. Bipolar sensing in the right atrium may be implemented, for example, by sensing voltages developed between the A-tip 256 and the A-ring 254. Unipolar sensing may be implemented, for example, by sensing voltages developed between the A-tip 256 and the can electrode 309. Outputs from the right atrial sensing circuit are coupled to the control system 320.

A right ventricular sensing circuit 332 serves to detect and amplify electrical signals from the right ventricle of the heart. The right ventricular sensing circuit 332 may include, for example, a right ventricular rate channel 333 and a right ventricular shock channel 334. Right ventricular cardiac signals sensed through use of the RV-tip 212 electrode are right ventricular near-field signals and are denoted RV rate channel signals. A bipolar RV rate channel signal may be sensed as a voltage developed between the RV-tip 212 and the RV-ring. Alternatively, bipolar sensing in the right ventricle may be implemented using the RV-tip electrode 212 and the RV-coil 214. Unipolar rate channel sensing in the right ventricle may be implemented, for example, by sensing voltages developed between the RV-tip 212 and the can electrode 309.

Right ventricular cardiac signals sensed through the use of defibrillation electrodes are far-field signals, also referred to as RV morphology or RV shock channel signals. More particularly, a right ventricular shock channel signal may be detected as a voltage developed between the RV-coil 214 and the SVC-coil 216. A right ventricular shock channel signal may also be detected as a voltage developed between the RV-coil 214 and the can electrode 309. In another configuration the can electrode 309 and the SVC-coil electrode 216 may be electrically shorted and a RV shock channel signal may be detected as the voltage developed between the RV-coil 214 and the can electrode 309/SVC-coil 216 combination.

Outputs from the right ventricular sensing circuit 332 are coupled to the control system 320. In one embodiment of the invention, rate channel signals and shock channel signals may be used to develop morphology templates for analyzing cardiac signals. In this embodiment, rate channel signals and shock channel signals may be transferred from the right ventricular sensing circuit 332 to the control system 320 and to a template processor 324 where the morphological characteristics of a cardiac signal are analyzed. The template processor 324 works in combination with the control system 320 and the memory 370 to generate and maintain various types of templates, including, for example, templates used for arrhythmia discrimination.

Left atrial cardiac signals may be sensed through the use of one or more left atrial electrodes 215, 218, which may be configured as epicardial electrodes. A left atrial sensing circuit 335 serves to detect and amplify electrical signals from the left atrium of the heart. Bipolar sensing and/or pacing in the left atrium may be implemented, for example, using the extracardiac atrial electrodes 215 and 218. Unipolar sensing and/or pacing of the left atrium may be accomplished, for example, using the LA distal electrode 218 to can vector 309 or the LA proximal electrode 215 to can vector 309.

A left ventricular sensing circuit 336 serves to detect and amplify electrical signals from the left ventricle of the heart. Bipolar sensing in the left ventricle may be implemented, for example, by sensing voltages developed between the LV distal electrode 213 and the LV proximal electrode 217. Unipolar sensing may be implemented, for example, by sensing voltages developed between the LV distal electrode 213 or the LV proximal electrode 217 to the can electrode 309.

Optionally, an LV coil electrode (not shown) may be inserted into the patient's cardiac vasculature, e.g., the coronary sinus, adjacent the left heart. Signals detected using combinations of the LV electrodes, 213, 217, LV coil electrode (not shown), and/or can electrodes 309 may be sensed and amplified by the left ventricular sensing circuitry 336. The output of the left ventricular sensing circuit 336 is coupled to the control system 320.

The outputs of the switching matrix 310 may be operated to couple selected combinations of electrodes 211, 212, 213, 214, 215, 216, 217, 218, 256, 254 to an evoked response sensing circuit 337. The evoked response sensing circuit 337 serves to sense and amplify voltages developed using various combinations of electrodes for providing capture threshold information for selecting pacing electrode configurations for enhancing rhythm management performance in accordance with embodiments of the invention.

The pacemaker control circuit 322, in combination with pacing circuitry for the left atrium, right atrium, left ventricle, and right ventricle 341, 342, 343, 344, may be implemented to selectively generate and deliver pacing pulses to the heart using various electrode combinations.

For right ventricular pacing, bipolar pacing may be delivered using the RV-tip electrode 212 and the RV-ring electrode 211. Unipolar pacing may be delivered using the RV-tip 212 to can 309 vector.

In an example of left ventricular pacing, bipolar pacing pulses may be delivered to the left ventricle between the LV distal electrode 213 and the LV proximal electrode 217. In another example, unipolar pacing pulses may be delivered to the left ventricle, for example, between the LV distal electrode 213 and the can 309. The cardiac signal following the delivery of the pacing pulses may preferably be sensed using the LV proximal electrode 217 and the can 309.

In an example of right atrial pacing, bipolar pacing pulses may be delivered to the right atrium between the A-tip electrode 256 and the A-ring electrode 254. In another example, unipolar pacing pulses may be delivered to the right atrium, for example, between the A-tip electrode 256 and the can electrode 309.

In an example of left atrial pacing, bipolar pacing pulses may be delivered to the left atrium between the LA distal electrode 218 and the LA proximal electrode 215. In another example, unipolar pacing pulses may be delivered to the left atrium, for example, between the LA distal electrode 218 and the can electrode 309. The cardiac signal following the delivery of the pacing pulses can be used for comparing and selecting electrode configurations and can be sensed using the A-tip 256 to A-ring 254 vector.

In one embodiment of the invention, a switching matrix 310 is coupled to the A-tip 256, A-ring 254, RV-tip 212, RV-coil 214, LV distal electrode 213, LV proximal electrode 217, SVC coil 216, extracardiac left atrial electrodes 215 and 218, indifferent, and can 309 electrodes. The switching matrix 310 may be arranged to provide connections to various configurations of pacing and defibrillation electrodes. The outputs of the switching matrix 310 are coupled to capture detection circuitry 337 that determines cardiac responses to pacing pulses.

Pacing electrode selection processor 323 includes circuitry configured to compare capture threshold data and other data for selection of pacing lead configurations. In further embodiments of the invention, lead impedance data can be sensed using lead impedance sensor 325 and P-wave and R-wave amplitude can be sensed using P-wave and R-wave amplitude sensor 326. Pacing electrode selection processor 323 can use data from both lead impedance sensor 325 and P-wave and R-wave amplitude sensor 326, along with capture threshold information to select an electrode configuration. For example, lead impedance data collected over time can indicate electrode dislodgement and/or when the quality of a lead/tissue interface is deteriorating. In instances where the lead impedance sensor 325 senses increased lead impedance, the pacing electrode selection processor 323 take lead impedance into account in the pacing electrode configuration selection process.

Pacing electrode selection processor can be communicatively coupled to an advanced patient management (APM) system or display devices (not shown) directly or via telemetry circuitry 360. Information related to pacing electrode configurations can thus be communicated and displayed for further patient treatment or diagnosis. In some embodiments, the capture threshold data collected by an implantable device may be transmitted to an APM system for analysis and automatic pacing electrode selection. In one implementation, the patient's physician may access and evaluate patient data transmitted from the CRM device to the patient information server. After evaluation of the patient data, the patient's physician may communicate with the CRM through the APM system to initiate, terminate, or modify the therapy functions, including pacing electrode selection processes of the CRM device. Systems and methods involving advanced patient management techniques are further described in U.S. Pat. Nos. 6,336,903, 6,312,378, 6,270,457, and 6,398,728, incorporated herein by reference.

Selecting alternate electrode configurations in accordance with embodiments of the invention may allow pacing at lower pacing thresholds. The battery longevity of a CRM device can thus be increased because the CRM device can consistently pace at a lower energy level. Lead impedance data and P-wave and R-wave amplitude measurement information can be used to supplement pacing threshold in pacing electrode configuration selection.

Methods, devices, and systems in accordance with the present invention may incorporate one or more of the features, structures, methods, or combinations thereof described herein. For example, a medical system may be implemented to include one or more of the described features and/or processes. It is intended that such a method, device, or system need not include all of the features and functions described herein, but may be implemented to include one or more selected features and/or functions that provide unique structures and/or functionality.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for selecting an electrode configuration for pacing, comprising:

delivering one or more pacing pulses to a first heart chamber during normal pacing using a primary pacing electrode configuration;

automatically triggering a first capture threshold test;

selecting a first alternative pacing electrode configuration for use during the first capture threshold test;

delivering one or more pacing pulses using the first alternative pacing electrode configuration during an entire duration of the first capture threshold test;

collecting capture threshold data associated with the first alternative pacing electrode configuration during the first capture threshold test;

after determining a capture threshold of the first alternative pacing electrode configuration, resuming normal pacing;

after resuming the normal pacing, automatically triggering a second capture threshold test;

selecting a second alternative pacing electrode configuration different from the first alternative electrode combination for use in the second capture threshold test;

delivering one or more pacing pulses using the second alternative pacing electrode configuration during an entire duration of the second capture threshold test;

collecting capture threshold data associated with the second alternative pacing electrode configuration during the second capture threshold test;

determining whether a sufficient amount of alternative electrode data has been acquired;

in response to a determination that a sufficient amount of alternative electrode data has been acquired, comparing the collected capture threshold data associated with the first alternative pacing electrode, the collected capture threshold data associated with the second alternative pacing electrode configuration, and capture threshold data associated with the primary pacing electrode configuration; and selecting a pacing electrode configuration based on the comparison.

2. The method of claim 1, further comprising:

collecting lead impedance data; and selecting the pacing electrode configuration using the lead impedance data.

3. The method of claim 1, further comprising:
collecting cardiac signal amplitude measurement data; and
selecting the pacing electrode configuration using the cardiac signal amplitude measurement data.

4. The method of claim 1, wherein delivering the one or more pacing pulses using the first alternative pacing electrode configuration comprises:
using a unipolar electrode configuration in response to the primary pacing electrode configuration having a bipolar configuration; and
using a bipolar electrode configuration in response to the primary pacing electrode configuration having a unipolar configuration.

5. The method of claim 1, wherein selecting the pacing electrode configuration comprises comparing both of the capture threshold data associated with the first alternative electrode configuration and the capture threshold data associated with the second alternative electrode configuration with the capture threshold data associated with the primary pacing electrode configuration.

6. A system for selecting a pacing electrode configuration, comprising:
a plurality of electrodes configured to electrically couple to a heart, wherein the plurality of electrodes are configurable to include a primary pacing electrode configuration, a first alternative electrode configuration, and a second alternative pacing electrode configuration;
a pulse generator coupled to the plurality of electrodes, the pulse generator configured to deliver electrical stimulation pulses to the heart using configurations of the plurality of electrodes; and
a processor configured to
collect capture threshold data associated with the first alternative pacing electrode configuration during an entire duration of a first capture threshold test,
collect capture threshold data associated with the second alternative pacing electrode configuration during an entire duration of a second capture threshold test,
resume normal pacing between the first and second capture threshold tests,
determine whether a sufficient amount of alternative electrode data has been acquired,
in response to a determination that a sufficient amount of alternative electrode data has been acquired, compare the collected capture threshold data associated with the first capture threshold test, the collected capture threshold data associated with the second capture threshold test, and capture threshold data associated with the primary pacing electrode configuration, and
select a pacing electrode configuration based on the comparison.

7. The system of claim 6, wherein the processor comprises at least one implantable component.

8. The system of claim 6, wherein the processor is further configured to collect lead impedance data and to select the pacing electrode configuration based on the lead impedance data.

9. The system of claim 6, wherein the processor is further configured to collect cardiac signal amplitude data and to select the pacing electrode configuration based on the cardiac signal amplitude data.

10. The system of claim 6, wherein the pulse generator is configured to deliver safety pulses using the primary pacing electrode configuration during one or both of the first and the second capture threshold tests.

11. The system of claim 6, wherein the processor is configured to select the first alternative pacing electrode configuration as a unipolar electrode configuration in response to the primary pacing electrode configuration having a bipolar configuration.

12. The system of claim 6, wherein the processor is configured to select the first alternative pacing electrode configuration as a bipolar electrode configuration in response to the primary pacing electrode configuration having a unipolar configuration.

13. A system for selecting an electrode configuration for pacing, comprising:
means for delivering one or more pacing pulses to a first heart chamber during normal pacing using a primary pacing electrode configuration;
means for performing a first capture threshold test using a first alternative pacing electrode configuration during an entire duration of the first capture threshold test, and for performing a second capture threshold test using a second alternative pacing electrode configuration during an entire duration of the second capture threshold test, the first and second capture threshold tests separated by a period of normal pacing;
means for collecting capture threshold data associated with the first alternative pacing electrode configuration during the first capture threshold test and collecting capture threshold data associated with the second alternative pacing electrode configuration during the second capture threshold test;
means for determining whether a sufficient amount of alternative electrode data has been acquired;
means for comparing, in response to a determination that a sufficient amount of alternative electrode data has been acquired, the collected capture threshold data associated with the first alternative pacing electrode configuration, the collected capture threshold data associated with the second alternative pacing electrode configuration, and capture threshold data associated with the primary pacing electrode configuration; and
means for selecting a pacing electrode configuration based on the comparison.

14. The system of claim 13, further comprising means for selecting the first alternative pacing electrode configuration as a unipolar configuration in response to the primary pacing electrode having a bipolar configuration and for selecting the first alternative pacing electrode configuration as a bipolar configuration in response to the primary pacing electrode configuration having a unipolar configuration.

* * * * *

UNITED STATES PATENT AND TRADEMARK OFFICE
CERTIFICATE OF CORRECTION

PATENT NO.       : 7,647,108 B2                                    Page 1 of 1
APPLICATION NO.  : 10/955393
DATED            : January 12, 2010
INVENTOR(S)      : Scott M. Freeberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this

Sixteenth Day of November, 2010

David J. Kappos
*Director of the United States Patent and Trademark Office*